United States Patent
Krüger et al.

(10) Patent No.: US 6,271,226 B1
(45) Date of Patent: Aug. 7, 2001

(54) OXIME DERIVATIVES AND THEIR USE AS FUNGICIDES

(75) Inventors: Bernd-Wieland Krüger, Gladbach; Peter Gerdes, Aachen; Herbert Gayer, Monheim; Ralf Tiemann, Leverkusen; Stefan Dutzmann, Langenfeld; Klaus Stenzel, Düsseldorf; Gerd Hänssler, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/284,367

(22) PCT Filed: Oct. 6, 1997

(86) PCT No.: PCT/EP97/05475

§ 371 Date: Apr. 14, 1999

§ 102(e) Date: Apr. 14, 1999

(87) PCT Pub. No.: WO98/17653

PCT Pub. Date: Apr. 30, 1998

(30) Foreign Application Priority Data

Oct. 17, 1996 (DE) ............................................. 196 42 864

(51) Int. Cl.[7] ........................ C07D 273/00; A01N 43/72
(52) U.S. Cl. ........................ 514/229.2; 544/65; 548/125
(58) Field of Search ............... 548/124; 544/65; 514/229.2

(56) References Cited

U.S. PATENT DOCUMENTS 5,679,676 * 10/1997 Kruger ............................. 514/229.2

FOREIGN PATENT DOCUMENTS

| 4442732 | 6/1996 | (DE) . |
| WO 9504728 | 2/1995 | (WO) . |
| WO 9625406 | 8/1996 | (WO) . |

* cited by examiner

*Primary Examiner*—Robert Gerstl
(74) *Attorney, Agent, or Firm*—Norris McLaughlin & Marcus

(57) ABSTRACT

The invention relates to novel oxime derivatives of formula (I), in which A stands for alkadiyl, Ar for optionally substituted aryls or heteroaryls respectively, G for a single bond, optionally an alkandiyl interrupted by heteroatoms (in which nonetheless the carbon atom is bound to $R^1$, and is always bound to a carbon atom of the alkandiyl chain) or a grouping, $R^3$—O—N=C= wherein $R^3$ stands for alkyl, $R^1$ respectively for hydrogen, cyano or substituted alkyl, alkoxy, alkylthio, alkylamino or cycloalkyl, $R^2$ stands for hydrogen or alkyl, Y stands for oxygen, sulfur or NH, and Z stands respectively for optionally substituted alkyl, alkenyl, alkinyl, cycloalkyl, aryl or heterocyclyl, to a method for their production and their use as fungicides, as well as to new intermediate products and multiple methods for their production.

15 Claims, No Drawings

OXIME DERIVATIVES AND THEIR USE AS FUNGICIDES

This application is a 371 of PCT/EP97/05475, which was filed on Oct. 6, 1997.

The invention relates to novel oxime derivatives, to a plurality of processes for their preparation and to their use as fungicides, and also to novel intermediates and to a plurality of processes for their preparation.

It is already known that certain oxime derivatives which are constitutionally similar to those described below have fungicidal properties (cf., for example, WO-A 9504728). However, in many instances the fungicidal activity of these compounds is unsatisfactory.

This invention, accordingly, provides the novel oxime derivatives of the general formula (I)

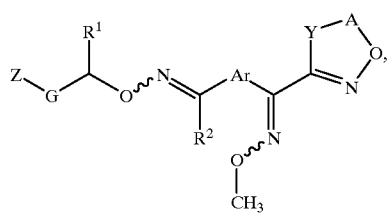
(I)

in which
- A represents alkanediyl
- Ar represents in each case optionally substituted arylene or heteroarylene,
- G represents a single bond, alkanediyl which is optionally interrupted by hetero atoms (but where the carbon atom to which $R^1$ is attached is in each case linked with a carbon atom of the alkanediyl chain) or a grouping

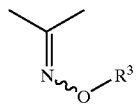

in which
- $R^3$ represents alkyl,
- $R^1$ represents hydrogen, cyano or in each case optionally substituted alkyl, alkoxy, alkylthio, alkylamino, dialkylamino or cycloalkyl,
- $R^2$ represents hydrogen or alkyl,
- Y represents oxygen, sulphur or —NH— and
- Z represents in each case optionally substituted alkyl, alkenyl, alkinyl, cycloalkyl, aryl or heterocyclyl.

In the definitions, the saturated or unsaturated hydrocarbon chains, such as alkyl, alkanediyl, alkenyl or alkinyl, are in each case straight-chain or branched, also attached to hetero atoms, such as in alkoxy, alkylthio or alkylamino. If an alkyl or alkanediyl chain is interrupted by more than one hetero atom, these are identical or different. If an alkyl or alkanediyl chain is interrupted by more than one oxygen atom, these are not adjacent to one another.

Halogen generally represents fluorine, chlorine, bromine or iodine, and also pseudohalogens, such as, for example, cyano, preferably fluorine, chlorine, bromine or cyano, in particular fluorine or chlorine.

Aryl represents aromatic mono or polycyclic hydrocarbon rings, such as, for example, phenyl, naphthyl, anthranyl, phenanthryl, preferably phenyl or naphthyl, in particular phenyl.

Heterocyclyl represents saturated or unsaturated, and also aromatic, cyclic compounds in which at least one ring member is a hetero atom, i.e. an atom which differs from carbon. If the ring contains a plurality of hetero atoms, these may be identical or different. Preferred hetero atoms are oxygen, nitrogen or sulphur. If appropriate, the cyclic compounds form, together with other carbocyclic or heterocyclic, fused-on or bridged rings, a polycyclic ring system. Preference is given to mono- or bicyclic ring systems, in particular to mono- or bicyclic aromatic ring systems.

Cycloalkyl represents saturated carbocyclic cyclic compounds which optionally form a polycyclic ring system with other carbocyclic fused-on or bridged rings.

Furthermore, it has been found that the novel oxime derivatives of the general formula (I) are obtained when (process a)) oximes of the general formula (II)

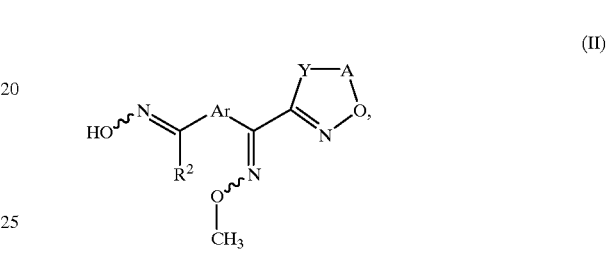
(II)

in which
- A, Ar, Y and $R^2$ are as defined above, are reacted with an alkylating agent of the general formula (III)

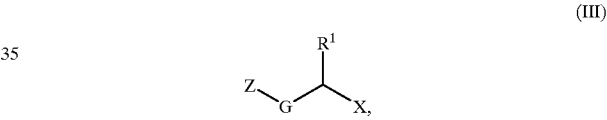
(III)

in which
- G, $R^1$ and Z are as defined above and
- X represents halogen, alkylsulphonyloxy or optionally substituted arylsulphonyloxy, if appropriate in the presence of a diluent and if appropriate in the presence of an acid acceptor.

Finally, it has been found that the novel oxime derivatives of the general formula (I) have a very strong fungicidal activity.

If appropriate, the compounds according to the invention can be present as mixtures of various possible isomeric forms, in particular of stereoisomers, such as, for example, E and Z, or optical isomers. What is claimed are both the E and the Z isomers, the individual enantiomers, the racemates and also any mixtures of these isomers.

The present application preferably provides oxime derivatives of the formula (I) in which
- A represents alkanediyl having 1 to 6 carbon atoms,
- Ar represents in each case optionally substituted phenylene or naphthylene, represents mono- or bicyclic heteroarylene having in each case 5 or 6 ring members or represents benzo-fused heteroarylene having 5 or 6 ring members at least one of which in each case represents oxygen, sulphur or nitrogen and one or two others optionally represent nitrogen, where the possible substituents are preferably selected from the list below: halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl having in each case 1 to 6 carbon atoms, in each case straight-chain or branched alkenyl, alkenyloxy or alkinyloxy having in each case 2 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched halogenoalkenyl or halogenoalkenyloxy having in each case 2 to 6 carbon atoms and 1 to 11 identical or different halogen atoms, in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, in each case doubly attached alkylene or dioxyalkylene having in each case 1 to 6 carbon atoms and being in each case optionally mono- or polysubstituted by identical or different substituents selected from the group consisting of halogen, straight-chain or branched alkyl having 1 to 4 carbon atoms and straight-chain or branched halogenoalkyl having 1 to 4 carbon atoms and 1 to 9 identical or different halogen atoms, G represents a single bond, represents alkanediyl having 1 to 5 chain members which is optionally interrupted by one or two heteroatoms (but where the carbon atom to which $R^1$ is attached is in each case linked to a carbon atom of the alkanediyl chain) or a grouping

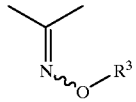

in which
  $R^3$ represents alkyl having 1 to 4 carbon atoms,
  $R^1$ represents hydrogen, cyano, represents in each case optionally halogen-, cyano- or $C_1$–$C_4$-alkoxy-substituted alkyl, alkoxy, alkylthio, alkylamino or dialkylamino having in each case 1 to 6 carbon atoms in the alkyl groups or represents in each case optionally halogen-, cyano-, carboxyl-, $C_1$–$C_4$-alkyl- or $C_1$–$C_4$-alkoxy-carbonyl-substituted cycloalkyl having 3 to 6 carbon atoms,
  $R^2$ represents hydrogen or alkyl having 1 to 4 carbon atoms,
  Y represents oxygen, sulphur or —NH— and
  Z represents alkyl having 1 to 8 carbon atoms which is optionally mono- or polysubstituted by an identical or different substituent selected from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl (each of which may optionally be substituted by halogen);
  represents in each case optionally halogen-substituted alkenyl or alkinyl having in each case up to 8 carbon atoms;
  represents cycloalkyl having 3 to 6 carbon atoms which is in each case optionally mono- or polysubstituted by identical or different substituents selected from the group consisting of halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl and $C_1$–$C_4$-alkoxy-carbonyl;
  or represents phenyl, naphthyl, each of which is optionally mono- or polysubstituted by identical or different substituents, or represents heterocyclyl having 3 to 7 ring members at least one of which represents oxygen, sulphur or nitrogen and one or two others optionally represent nitrogen, where the possible substituents are preferably selected from the list below:
    halogen, cyano, nitro, amino, hydroxyl, formyl, carboxyl, carbamoyl, thiocarbamoyl;
    in each case straight-chain or branched alkyl, alkoxy, alkylthio, alkylsulphinyl or alkylsulphonyl having in each case 1 to 6 carbon atoms;
    in each case straight-chain or branched alkenyl or alkenyloxy having in each case 2 to 6 carbon atoms;
    in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
    in each case straight-chain or branched halogenoalkenyl or halogenoalkenyloxy having in each case 2 to 6 carbon atoms and 1 to 11 identical or different halogen atoms;
    in each case straight-chain or branched alkylamino, dialkylamino, alkylcarbonyl, alkylcarbonyloxy, alkoxycarbonyl or alkylsulphonyloxy having in each case 1 to 6 carbon atoms in the individual alkyl moieties;
    in each case doubly attached alkylene or dioxyalkylene having in each case 1 to 6 carbon atoms and being in each case optionally mono- or polysubstituted by identical or different substituents selected from the group consisting of halogen, straight-chain or branched alkyl having 1 to 4 carbon atoms and straight-chain or branched halogenoalkyl having from 1 to 4 carbon atoms and 1 to 9 identical or different halogen atoms;
    cycloalkyl having 3 to 6 carbon atoms;
    heterocyclyl or heterocyclyl-methyl having in each case 3 to 7 ring members,
    1 to 3 of which are in each case identical or different heteroatoms—in particular nitrogen, oxygen and/or sulphur- or a grouping

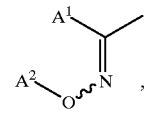

in which
  $A^1$ represents alkyl having 1 to 4 carbon atoms or cycloalkyl having 1 to 6 carbon atoms and
  $A^2$ represents optionally cyano-, alkoxy-, alkylthio-, alkylamino-, dialkylamino- or phenyl-substituted alkyl having 1 to 4 carbon atoms, alkenyl or alkinyl having in each case 2 to 4 carbon atoms.

The present application in particular relates to compounds of the formula (I) in which
  A represents methylene, ethane-1,1-diyl, ethane-1,2-diyl, propane-1,1-diyl, propane-1,2-diyl, propane-1,3-diyl, propane-2,2-diyl, butane-1,2-diyl, butane-1,3-diyl or butane-2,3-diyl, Ar represents ortho-, meta- or para-phenylene, furandiyl, thiophenediyl, pyrrolediyl, pyrazolediyl, triazolediyl, oxazolediyl, isoxazolediyl, thiazolediyl, isothiazolediyl, oxadiazolediyl, thiadiazolediyl, pyridinediyl (in particular pyridine-2,3-diyl), pyrimidinediyl, pyridazinediyl, pyrazinediyl, 1,3,4-triazinediyl or 1,2,3-triazinediyl, each of which is optionally mono- or disubstituted by fluorine, chlorine, cyano, methyl, ethyl, cyclopropyl, trifluoromethyl, methoxy, ethoxy, methylthio, methylsulphinyl or methylsulphonyl, G represents a single bond, methylene, ethane-1,2-diyl, —O—CH$_2$— or a grouping

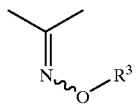

in which
R$^3$ represents methyl, ethyl, n- or i-propyl,
R$^1$ represents hydrogen, cyano, methyl, ethyl or cyclopropyl,
R$^2$ represents hydrogen or methyl,
Y represents oxygen, sulphur or —NH— and
Z represents phenyl, 1,2,4-thiadiazolyl, 1,3,4-thiadiazolyl, 1,2,4-oxadiazolyl, 1,3,4-oxadiazolyl, pyridinyl, pyrimidyl, pyridazinyl, pyrazinyl, 1,2,3-triazinyl, 1,2,4-triazinyl, 1,3,5-triazinyl or 5,6-dihydro-1,4,2-dioxazinyl, each of which is optionally mono- to trisubstituted by identical or different substituents, where the possible substituents are preferably selected from the list below:
fluorine, chlorine, bromine, cyano, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloro-methylthio, trifluoromethylsulphinyl or trifluoromethylsulphonyl, methoxycarbonyl, ethoxycarbonyl,
in each case doubly attached methylenedioxy, ethylenedioxy, each of which is optionally mono- to tetrasubstituted by identical or different substituents selected from the group consisting of fluorine, chlorine, methyl,
trifluoromethyl and ethyl or a grouping

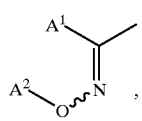

where
A$^1$ represents methyl, ethyl, n- or i-propyl, n-, i-, s- or t-butyl, cyclopropyl or cyclobutyl and
A$^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

A particularly preferred group of compounds according to the invention are those compounds of the formula (I) in which
A represents methylene, ethane-1,1-diyl, ethane-1,2-diyl, propane-1,1-diyl, propane-1,2-diyl, propane-1,3-diyl, propane-2,2-diyl, butane-1,2-diyl, butane-1,3-diyl or butane-2,3-diyl,
Ar represents ortho-phenylene, pyridine-2,3-diyl or thiophene-2,3-diyl,
G represents a single bond, methylene, ethane-1,2-diyl, —O—CH$_2$— or a grouping

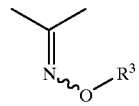

in which
R$^3$ represents methyl,
R$^1$ represents methyl,
R$^2$ represents hydrogen,
Y represents oxygen, sulphur or —NH— and
Z represents phenyl, pyridyl, pyrimidyl, thienyl or 5,6-dihydro-1,4,2-dioxazinyl, each of which is optionally mono- to trisubstituted by identical or different substituents, where the possible substituents are preferably selected from those below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl,
in each case doubly attached methylenedioxy or ethylenedioxy, each of which is optionally mono- to tetrasubstituted by identical or different substituents selected from the group consisti of fluorine, chlorine, methyl, trifluoromethyl and ethyl or a grouping

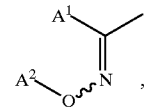

in which
A$^1$ represents methyl, ethyl, n- or i-propyl, n-, i-, s- or t-butyl, cyclopropyl or cyclobutyl and
A$^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

In a very particularly preferred group of compounds according to the invention, Ar represents o-phenylene.

In a further very particularly preferred group of compounds according to the invention, Y represents oxygen and A represents 1,2-ethanediyl.

The abovementioned general radical definitions or radical definitions given in the preferred ranges apply both to the end products of the formula (I) and correspondingly to the starting materials or intermediates required in each case for the preparation.

The radical definitions given for these radicals in the individual case, in the combinations or preferred combinations of radicals in question, are also replaced by any radical definitions of other preferred ranges, independently of the combination given in the particular case.

Examples of compounds according to the invention are listed in Tables 1 to 6:

TABLE 1

(I-a)

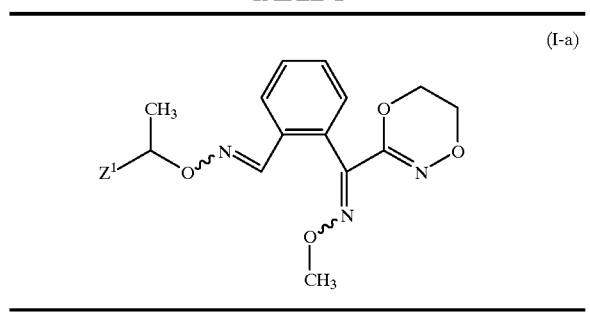

where $Z^1$ represents the following substituents:

TABLE 2

(I-a)

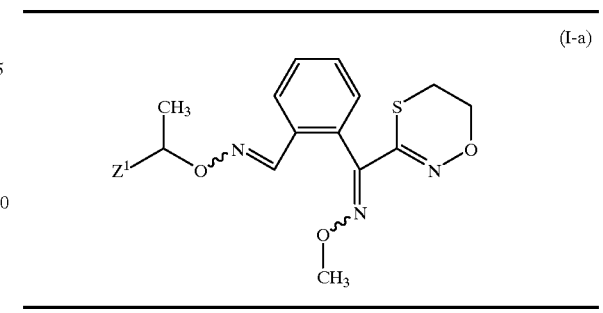

where $Z^1$ represents the substituents mentioned in Table 1.

TABLE 3

(I-a)

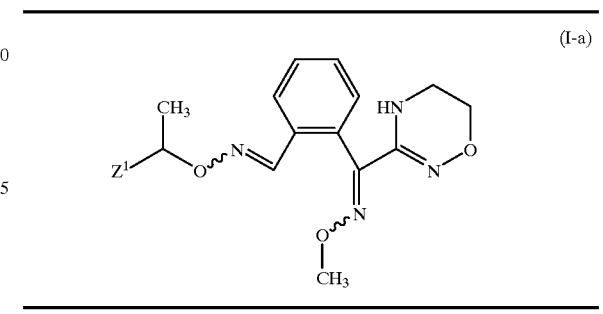

where $Z^1$ represents the substituents mentioned in Table 1.

TABLE 4

(I-a)

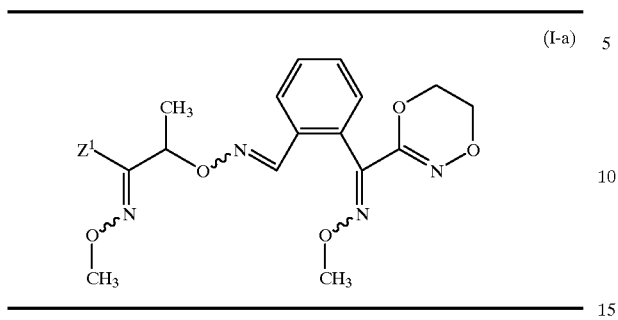

where $Z^1$ represents the substituents mentioned in Table 1.

TABLE 5

(I-a)

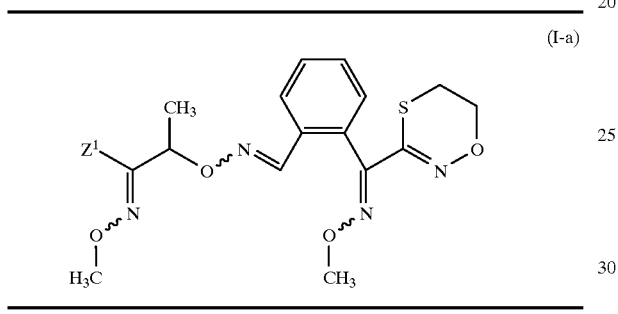

where $Z^1$ represents the substituents mentioned in Table 1.

TABLE 6

(I-a)

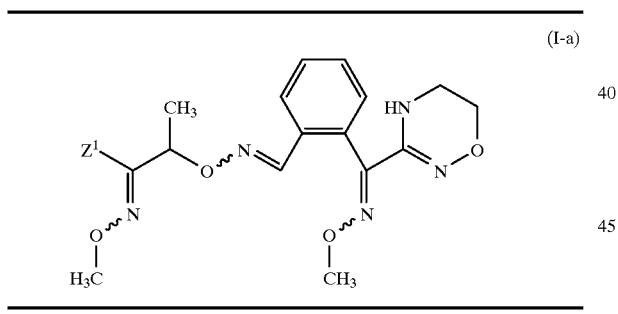

where $Z^1$ represents the substituents mentioned in Table 1.

The formula (II) provides a general definition of the oximes required as starting materials for carrying out the process a) according to the invention. In this formula (II), A, Ar, Y and $R^2$ preferably or in particular have those meanings which have already been mentioned in connection with the description of the compounds of the formula (I) according to the invention as being preferred or as being particularly preferred for A, Ar, Y and $R^2$.

The starting materials of the formula (II) have hitherto not been known, as novel substances, they also form part of the subject-matter of the present application.

The oximes of the formula (II) are obtained when (process b)) keto compounds of the general formula (IV)

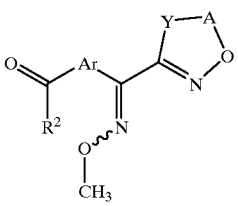

(IV)

in which

A, Ar, Y and $R^2$ are as defined above, are reacted with hydroxylamine or a salt thereof, if appropriate in the presence of a diluent, preferably an alcohol, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water and if appropriate in the presence of a base, preferably an alkaline earth metal or alkali metal hydroxide, alkoxide, acetate, carbonate or bicarbonate, such as, for example, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, or a tertiary amine, such as trimethylamine, triethylaamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The formula (IV) provides a general definition of the keto compounds required as starting materials for carrying out the process b) according to the invention. In this formula (IV), A, Ar, Y and $R^2$ preferably or in particular have those meanings which have already been mentioned in connection with the description of the compounds of the formula (I) according to the invention as being preferred or as being particularly preferred for A, Ar, Y and $R^2$.

The keto compounds of the formula (IV) have hitherto not been known, as novel substances, they also form part of the subject-matter of the present application.

The keto compounds of the formula (IV) are obtained when (process c)) halogenoalkyl compounds of the general formula (V)

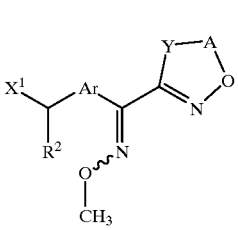

(V)

in which

A, Ar, Y and $R^2$ are as defined above, $X^1$ represents halogen, are reacted by known methods with dimethyl sulphoxide (Nef reaction), Urotropin (Sommelet reaction), a nitronic acid (Hass reaction), an amine oxide or a nitroso compound (Kröhnke reaction), if appropriate in the presence of a base, preferably of an alkaline earth metal or alkali metal hydride, amide, alkoxide, such as, for example, sodium hydride, sodium amide, sodium methoxide, sodium ethoxide, potassium tert-butoxide, and if appropriate in the presence of a diluent, preferably an amide, such as N,N-dimethylformamide, or an alcohol, such as methanol, ethanol, n- or i-propanol, n-, i-, sec- or tert-butanol, at temperatures of from −20 to 150° C., preferably from −10 to 120° C.

The formula (V) provides a general definition of the halogenoalkyl compounds required as starting materials for carrying out the process c) according to the invention. In this formula (V), A, Ar, Y and $R^2$ preferably or in particular have those meanings which have already been mentioned in connection with the description of the compounds of the formula (I) according to the invention as being preferred or as being particularly preferred for A, Ar, Y and $R^2$. $X^1$ represents halogen, and preferably represents chlorine or bromine.

The halogenoalkyl compounds of the formula (V) have hitherto not been known, as novel substances, they also form part of the subject-matter of the present application.

The halogenoalkyl compounds of the formula (V) are obtained when (process (d)) phenoxy compounds of the general formula (VI)

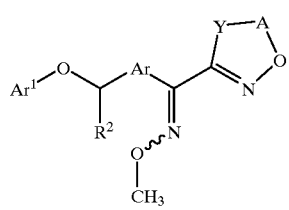

(VI)

in which

A, Ar, Y and $R^2$ are as defined above and $Ar^1$ represents optionally substituted aryl, are reacted with an acyl halide of the formula (VII)

E-$X^2$  (VII)

in which

E represents alkylcarbonyl, arylcarbonyl, alkylsulphonyl or arylsulphonyl and $X^2$ represents halogen, if appropriate in the presence of a diluent, and if appropriate in the presence of a Lewis acid.

The formula (VI) provides a general definition of the phenoxy compounds required as starting materials for carrying out process d) according to the invention. In this formula (VI), A, Ar, Y and $R^2$ preferably or in particular have those meanings which have already been mentioned in connection with the description of the compounds of the formula (I) according to the invention as being preferred or as being particularly preferred for A, Ar, Y and $R^2$. Arl represents optionally substituted aryl, preferably represents phenyl which is optionally substituted by halogen, alkyl or alkoxy having in each case 1 to 4 carbon atoms, in particular represents phenyl or 2-, 3- or 4-methylphenyl.

The phenoxy compounds of the formula (VI) are known and/or can be prepared by known methods (cf., for example, WO-A 9 504 728 and DE-A 19 504 625).

The formula (VII) provides a general definition of the acyl halides furthermore required as starting materials for carrying out the process d) according to the invention. In this formula (VII), $X^2$ represents halogen, preferably represents chlorine or bromine. E represents alkylcarbonyl, preferably acetyl, propionyl or pivaloyl, arylcarbonyl, preferably benzoyl or toluyl, alkylsulphonyl, preferably methylsulphonyl, or arylsulphonyl, preferably tolylsulphonyl.

The acyl halides of the formula (VII) are generally known chemicals for synthesis.

The starting materials furthermore required for carrying out the process c) according to the invention, such as dimethyl sulphoxide, Urotropin, nitronic acids, amine oxides or nitroso compounds, are generally known chemicals for synthesis.

The hydroxylamine or salts thereof furthermore required as starting material for carrying out the process b) and e) according to the invention are generally known chemicals for synthesis.

The formula (III) provides a general definition of the alkylating agents furthermore required as starting materials for carrying out the process a) according to the invention. In the formula (III), G and Z preferably or in particular have those meanings which have already been mentioned in connection with the description of the compounds of the formula (I) according to the invention as being preferred or as being particularly preferred for G and Z. X represents halogen, preferably chlorine, bromine, or iodine, or alkylsulphonyl, preferably methylsulphonyl, or optionally substituted arylsulphonyl, preferably 4-tolylsulphonyl.

Some of the alkylating agents of the general formula (III) are known, and they can be prepared by known processes. (cf., for example, J.Org.Chem., 51, 1, 1986, 109–111; J.Chem.Soc.Perkin Trans.2, 1986, 593–598).

Novel, and also part of the subject-matter of the present application, are the alkylating agents of the general formula (III-a)

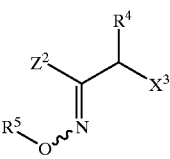

(III-a)

in which $R^4$ represents alkyl or cycloalkyl, $R^5$ represents alkyl, $X^3$ represents halogen and $Z^2$ represents optionally substituted aryl or heterocyclyl.

Preference is given to compounds of the formula (III-a) in which $R^4$ represents alkyl having 1 to 4 carbon atoms or cycloalkyl having 3 to 6 carbon atoms, $R^5$ represents alkyl having 1 to 4 carbon atoms, $X^3$ represents chlorine, bromine or iodine and $Z^2$ represents phenyl, naphthyl, each of which is optionally mono- or polysubstituted by identical or different substituents, or represents heterocyclyl having 3 to 7 ring members at least one of which represents oxygen, sulphur or nitrogen and one or two others optionally represent nitrogen, where the possible substituents are preferably selected from the list below:

halogen, cyano, nitro, amino, hydroxyl, formyl, carboxyl, carbamoyl, thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched halogenalkyl, halogenalkoxy, halogenoalkylthio, halogenalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl or alkylsulphonyloxy having in each case 1 to 6 carbon atoms in the individual alkyl moieties;

in each case doubly attached alkylene or dioxyalkylene having in each case 1 to 6 carbon atoms and being in each case optionally mono- or polysubstituted by identical or different substituents selected from the group consisting of halogen, straight-chain or branched alkyl having 1 to 4 carbon atoms and straight-chain or branched halogenoalkyl having from 1 to 4 carbon atoms and 1 to 9 identical or different halogen atoms;

cycloalkylalkyl having 3 to 6 carbon atoms; heterocyclyl or heterocyclyl-methyl having in each case 3 to 7 ring members, 1 to 3 of which are in each case identical or different heteroatoms in particular nitrogen, oxygen and/or sulphur—or a grouping

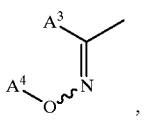

in which
A³ represents alkyl having 1 to 4 carbon atoms or cycloalkyl having 1 to 6 carbon atoms and
A⁴ represents optionally cyano-, alkoxy-, alkylthio-, alkylamino-, dialkylamino- or phenyl-substituted alkyl having 1 to 4 carbon atoms, alkenyl or alkinyl having in each case 2 to 4 carbon atoms.

Particular preference is given to compounds of the formula (III-a) in which
R⁴ represents methyl, ethyl or cyclopropyl,
R⁵ represents methyl or ethyl,
X³ represents chlorine or bromine and
Z² represents phenyl, pyridyl, pyrimidyl or thienyl, each of which is optionally mono- to trisubstituted by identical or different substituents, where the possible substituents are preferably selected from the list below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, in each case doubly attached methylenedioxy or ethylenedioxy, each of which is optionally mono- to tetrasubstituted by identical or different substituents selected from the group consisting of fluorine, chlorine, methyl, trifluoromethyl or a grouping

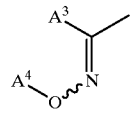

in which
A³ represents methyl, ethyl, n- or i-propyl, n-, i-, s- or t-butyl, cyclopropyl or cyclobutyl and
A⁴ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylarinoethyl or benzyl.

The alkylating agents of the formula (III-a) are obtained (process e)) when halogenoketone of the general formula (VIII)

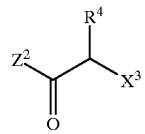

(VIII)

in which
R⁴, X³ and Z² are as defined above,
are reacted with hydroxylamine or a salt thereof, if appropriate in the presence of a diluent, preferably an an alcohol, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water and if appropriate in the presence of a base, preferably an alkaline earth metal or alkali metal hydroxide, alkoxide, acetate, carbonate or bicarbonate, such as, for example, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, or a tertiary amine, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The formula (III) provides a general definition of the halogenoketones required as starting materials for carrying out the process e) according to the invention. In the formula (III), R⁴, X³ and Z² preferably or in particular have those meanings which have already been mentioned in connection with the description of the compounds of the formula (III-a) according to the invention as being preferred or as being particularly preferred for R⁴, X³ and Z².

The halogenoketones of the formula (VIII) required as starting materials for carrying out the process e) according to the invention are generally known chemicals for synthesis.

Suitable diluents for carrying out the process a) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetarnide, N-methylformanilide, N-methylpyrrolidone or hexamethylphosphoric triamide; esters such as methyl acetate or ethyl acetate; sulphoxides, such as dimethyl sulphoxide, or sulphones, such as sulpholane.

If appropriate, process a) according to the invention is carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out process a) according to the invention, the reaction temperatures can be varied within a relatively wide range. In general, the reaction is carried out at temperatures from −20° C. to 150° C., preferably at temperatures from 0° C. to 80° C.

When carrying out the process a) according to the invention for preparing the compounds of the formula (I), generally 1 to 15 mol, preferably 1 to 8 mol, of alkylating agent of the formula (m) are employed per mole of the oxime of the formula (II).

The processes a), b), c), d) and e) according to the invention are generally carried out under atmospheric pressure. However, it is also possible to carry out the reaction under elevated or reduced pressure—generally between 0.1 bar and 10 bar.

The materials according to the invention have potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Psdeudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris pv. oryzae;*

Pseudomonas species, such as, for example, *Pseudomonas syringae pv. lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae,*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Altemaria species, such as, for example, *Alternaria brassicae;* and

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling cereal diseases, such as, for example, against Erysiphe species, for controlling diseases in viticulture and fruit and vegetable growing, such as, for example, against Venturia, Sphaerotheca, Podosphaera, Phytophthora and Plasmopara species, or for controlling rice diseases, such as, for example, against Pyricularia species. Cereal diseases, such as, for example, Septoria, Pyrenophora or Cochliobolus species, are also successfully controlled. Furthermore, the compounds according to the invention may also be employed to increase the yield of crops.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to use organic solvents as auxiliary solvents, for example. Suitable liquid solvents are essentially aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of suitable co-components in mixtures are the following compounds:

Fungicides: aldimorph, ampropylfos, ampropylfos potassium, andoprim, anilazine, azaconazole, azoxystrobin,
  benalaxyl, benodanil, benomyl, benzamacril, benzamacril-isobutyl, bialaphos, binapacryl, biphenyl, bitertanol, blasticdiin-S, bromuconazole, bupirimate, buthiobate,
  calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
  debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
  ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
  guazatine,
  bexachlorobenzene, hexaconazole, hymexazole,
  imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
  kasugamycin, kresoxim-methyl, copper preparations, such as: copper hydroxide, copper naphthenate, copper oxychloride, copper sulphate, copper oxide, oxine-copper and Bordeaux mixture,
  mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
  nickel dimethyldithiocarbamate, nitrothal-isopropyl, nuarimol,
  ofurace, oxadixyl, oxamocarb, oxolinic acid, oxycarboxim, oxyfenthiin,
  paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
  quinconazole, quintozene (PCNB),
  sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflurnizole, triforine, triticonazole, uniconazole, validamycin A, vinclozolin, viniconazole, zarilamide, zineb, ziram and also Dagger G,

OK-8705,

OK-8801,

α-( 1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol, α-(5-methyl-1,3-dioxan-5-yl)β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, isopropyl {2-methyl-1-[[[1-(4-methylphenyl) ethyl] amino] carbonyl] propyl}-carbamate-1, 1-(2,4-dichlorophenyl)-2-(1H-1,2,4-triazol-1-yl) ethanone-O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxarnide, 2,6-dichloro-5-(methylthio)-4-pyrimidinyl thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy4-O-(4-O-methyl-β-D-glycopyranosyl)-α-D-glucopyranosyl]-amino]-4-methoxy- 1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano-[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulfonamide, 4-methyl-tetrazolo[1,5-a]quinazolin-5(4H)-one, 8-(1,1-dimethylethyl)-N-ethyl-N-propyl-1,4-dioxaspiro [4.5]decane-2-methanarnine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)oxy]-2,5-thiophenedicarboxylate, cis-1-(4-chlorophenyl)-2-(1H-1,2,4-triazol-1-yl)-cycloheptanol, cis4-[3-[4-(1,1 -dimethylpropyl)-phenyl-2-methylpropyl]-2,6-dimethylmorpholine hydrochloride, ethyl [(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)4-methyl-3-nitro-benzenesulfonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetade, N-(6-methoxy)-3-pyridinyl)-cyclopropanecarboxamide, N-[2,2,2-trichloro-1-[(chloroacetyl)-amino]-ethyl]-benzamide, N-[3-chloro-4,5 -bis(2-propinyloxy)-phenyl]-N'-methoxy-methanimidamide, N-formyl-N-hydroxy-DL-alanine,-sodium salt, O,O-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-benzopyrane-2,1'(3'H)-isobenzofuran]-3'-one, Bactericides:

bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, acephate, acrinathrin, alanycarb, aldicarb, alphamethrin, amitraz, avermectin, AZ 60541, azadirachtin, azinphos A, azinphos M, azocyclotin, Bacillus thuringiensis, 4-bromo-2-(4-chlorophenyl)-1-(ethoxymethyl)-5-(tri-fluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lamda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

It is also possible to admix other known active compounds, such as herbicides, fertilizers and growth-promoting substances.

The active compounds can be used as such, in the form of their commercial formulations or the use forms prepared therefrom, such as ready-to-use solutions, suspensions, wettable powders, pastes, soluble powders, dusts and granules. They are used in the customary manner, for example by pouring, spraying, atomizing, spreading, foaming, brushing on and the like. It is further possible to apply the active compounds by the ultra-low volume method or to inject the active compound composition, or the active compound itself, into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the site of action.

PREPARATION EXAMPLES

Example 1

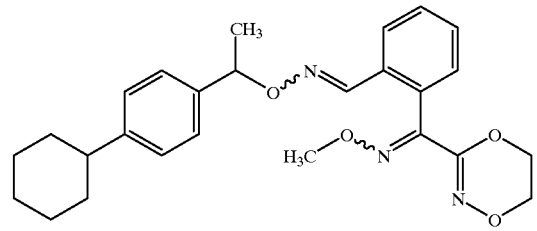

A solution of 0.5 g (1.9 mmol) of 2-[(5,6-dihydro-[1,4,2]dioxazin-3-yl)-methoxy-imino-methyl]-benzaldehyde oxime in 10 ml of dimethylformamide is cooled to 0° C. and, under argon, admixed with 0.063 g (2.1 mmol) of an 80% strength suspension of sodium hydride. A solution of 0.42 g (2.1 mmol) of 1-(1-chloroethyl)-4-cyclohexylbenzene in 2 ml of dimethylformamide is added dropwise to this mixture, which is stirred without any further cooling for 4 hours. The reaction mixture is poured into 150 ml of water and extracted 3 times with 100 ml of ethyl acetate each time. The combined organic phases are dried over magnesium sulphate and concentrated under reduced pressure. The residue is chromatographed over silica gel using cyclohexane/ethyl acetate (3:1). This gives 0.6 g (70% of theory) of 2-[(5,6-dihydro-[1,4,2]dioxazin-3-yl)-methoxyirninomethyl]-benzaldehyde O-[1-(4-cyclo-hexylphenyl)-ethyl] oxime.

$^1$H-NMR (CDC13, TMS): δ=1.20–1.40; 1.56; 1.59; 1.70–1.90; 2.48; 3.92; 4.07–4.16; 4.42–4.49; 5.30; 7.13–8.00 ppm.

Preparation of the Starting Material

Example II-1

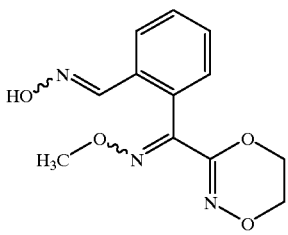

Under argon and at 20° C., a solution of 4 g (0.16 mol) of 2-[(5,6-dihydro-[1,4,2]dioxazin-3-yl)-methoxyimino-methyl]-benzaldehyde in 100 ml of ethanol is admixed with 5.5 g (0.08 mol) of hydroxylammonium chloride and 8 g (0.08 mol) of triethylamine, and the mixture is stirred at 20° C. for 2 hours. The mixture is poured into 500 ml of water and extracted three times with 100 ml of dichloromethane each time. The combined organic phases are dried over magnesium sulphate and concentrated under reduced pressure. The residue is chromatographed over silica gel using cyclohexane/ethyl acetate (4:1). This gives 2.4 g (57% of theory) of 2-[(5,6-dihydro-[1,4,2]dioxazin-3-yl)-methoxyimino-methyl]-benzaldehyde oxime.

$^1$H-NMR (CDC13, TMS): δ=3.97; 4.14–4.19; 4.49–4.52; 7.18–8.03 ppm.

Preparation of the Precursor

Example IV-1

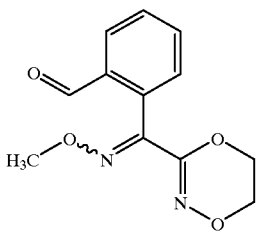

19.5 g (0.14 mol) of N-methylmorpholine N-oxide are added to a solution of 15 g (0.056 mol) of (2-chloromethylphenyl)-(5,6-dihydro-[1,4,2]dioxazin-3-yl)-methanone O-methyl oxime in 150 ml of dimethylformamide, and the mixture is stirred at 120° C. for 2 hours. After cooling, the mixture is poured into 1000 ml of water and extracted three times with 200 ml of ethyl acetate each time. The combined organic phases are dried over magnesium sulphate and concentrated under reduced pressure. The residue is stirred with diisopropyl ether and the resulting solid is filtered off with suction. This gives 10.5 g (76% of theory) of 2-[(5,6-dihydro-[1,4,2]dioxazin-3-yl)-methoxyimino-methyl]-benzaldehyde.

$^1$H-NMR (CDC13, TMS): δ=3.96; 4.17–4.20; 4.53–4.56; 7.29–7.95; 9.92 ppm.

Preparation of the Precursor

Example V-1

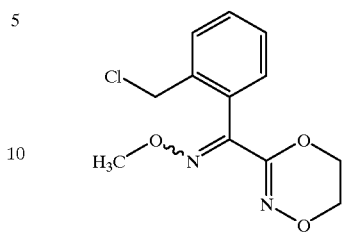

Over a period of 15 minutes, 61.1 g (0.775 mol) of acetyl chloride are added to a suspension of 103.4 g (0.775 mol) of anhydrous aluminium chloride in 1 l of dichloromethane. Under argon and at 20° C., a solution of 105 g (0.31 mol) of KBR[5896] in 500 ml of dichloromethane is added dropwise to this mixture, at which the reaction mixture warms to 30° C., and stirring is continued for a further 3 hours. The reaction mixture is poured onto 2 l of ice-water and extracted 3 times with 300 ml of dichloromethane each time. The combined organic phases are dried over magnesium sulphate and concentrated under reduced pressure. The residue is stirred with diiisopropyl ether and the resulting solid is filtered off with suction (59.1 g). The filtrate is concentrated under reduced pressure and the residue is chromatographed over silica gel using cyclohexane/ethyl acetate (3:1). This gives a further 4 g of product. Altogether, 63.1 g (76% of theory) of (2-chloromethyl-phenyl)-(5,6-dihydro-[1,4,2]dioxazin-3-yl)-methanone O-methyl oxime are obtained.

$^1$H-NMR (CDC13, TMS): δ=3.99; 4.174.20; 4.49–4.53; 7.15–7.53 ppm.

Example (2)

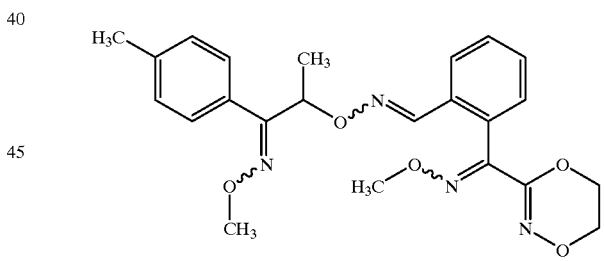

A solution of 0.4 g (1.52 mmol) of 2-[(5,6-dihydro-[1,4,2]dioxazin-3-yl)-methoxy-imino-methyl]-benzaldehyde oxime in 10 ml of dimethylformamide is cooled to 0° C. and, under argon, admixed with 0.055 g (1.82 mmol) of an 80% strength suspension of sodium hydride. A solution of 0.37 g (1.52 mmol) of 2-bromo-1-(p-tolyl)-propan-1-one O-methyl oxime in 2 mnl of dimethylformamide is added dropwise to this mixture, which is stirred without any further cooling for 4 hours. The reaction mixture is poured into 100 ml of water and extracted 3 times with 100 ml of ethyl acetate each time. The combined organic phases are dried over magnesium sulphate and concentrated under reduced pressure. The residue is chromatographed over silica gel using cyclohexane/ethyl acetate (3:1). This gives 0.42 g (63% of theory) of 2-[(5,6-dihydro-[1,4,2]dioxazin-3-yl)- methoxyimino-methyl]-benzaldehyde O-[2-methoxyimino-1-methyl-2-(p-tolyl)-ethyl] oxime.

1H-NMR (CDCl3, TMS): δ=1.56; 1.59; 2.32; 3.87; 3.99; 4.16; 4.48; 5.87; 7.11–7.98 ppm.

Preparation of the Starting Material

Example (III-a-1)

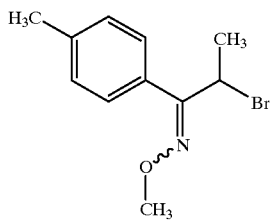

2.27 (10 mmol) of 2-bromo-1-(p-tolyl)-propan-1-one are dissolved in 10 ml of acetic acid and, at 20° C., admixed with 1.25 g (15 mmol) of hydroxylammonium chloride and 2.07 g (15 mmol) of sodium acetate. After 14 hours, the solvent is distilled off under reduced pressure, the residue is taken up in 100 ml of ethyl acetate and the organic phase is separated off, dried over 50 g of magnesium sulphate and concentrated. This gives 2.5 g (99% of theory) of 2-bromo-1-(p-tolyl)-propan-1-one O-methyl oxime as a mixture of isomers (e/z 70/30).

1H-NMR (DMSO-$d_6$, TMS): δ=1.69 (d, 3H, e isomer); 1,82 (d, 3H, z isomer); 3.78 (s, 3H, z isomer); 3.96 (s, 3H, e isomer) ppm.

By the method of Example (1), and in accordance with the general description of the preparation process a) according to the invention, it is also possible to obtain the compounds of the formula (I-a) according to the invention listed in Table 7 below:

TABLE 7

(I-a)

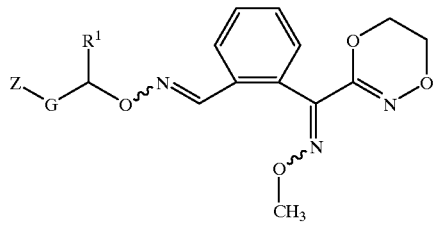

| Ex. No. | Z | G | R¹ | NMR*: |
|---|---|---|---|---|
| 3 | 3-Trifluoromethylphenyl | — | —CH3 | 1.61, D (2H); 3.92; 4.12, M (2H); 4.46, M (2H); 5.37, Q (1H); 7.14–8.02 |
| 4 | 4-Difluoromethoxyphenyl | — | —H | 3.93; 4.13, M (2H); 4.46, M (2H); 5.16; 6.50, T (1H); 7.10–8.00 |
| 5 | 4-Chlorophenyl | — | —CH3 | 1.57, D (3H); 3.93; 4.13, M (2H); 4.46, M (2H); 5.29, Q (1H); 7.13–8.02 |
| 6 | 4-Methylphenyl | — | —CH3 | 1.59, D (3H); 2.34; 3.93; 4.10, M (2H); 4.46, M (2H); 5.29, Q (1H); 7.13–8.01 |
| 7 | 4-Ethylphenyl | — | —CH3 | 1.23, T (3H); 1.60, D (3H); 2.64, Q (2H); 3.93; 4.10, M (2H); 4.45, M (2H); 5.30, Q (1H); 7.13–8.00 |
| 8 | 4-Phenoxyphenyl | — | —CH3 | 1.60, D (3H); 3.93; 4.13, M (2H); 4.47, M (2H); 5.33, Q (1H); 6.97–8.00 |
| 9 | 4-Propylphenyl | — | —CH3 | 0.94, T (3H); 1.59, D (3H); 1.66 M (2H); 2.57, T (2H); 3.92; 4.13, M (2H); 4.45, M (2H); 5.30, Q (1H); 7.13–8.00 |
| 10 | 4-i-Propylphenyl | — | —CH3 | 1.25, D (6H); 1.62, D (3H); 2.92, M (1H); 3.92; 4.11, M (2H); 4.45, M (2H); 5.33, Q (1H); 7.06–8.00 |
| 11 | 4-Bromophenyl | — | —CH3 | 1.56, D (3H); 3.93; 4.13, M (2H); 4.45, M (2H); 5.28, Q (1H); 7.13–8.00 |
| 12 | ![dioxazine] | — | —CH3 | 1.50, D (3H); 3.95; 4.10, M (2H); 4.15, M (2H); 4.37, M (2H); 4.53, M (2H); 4.75, Q (1H); 7.15–8.01 |

*The ¹H-NMR spectra were recorded in deuterochloroform (CDCl₃) or hexadeuterodimethyl sulphoxide (DMSO-$d_6$) using tetramethylsilane (TMS) as internal standard. The chemical shift is stated as δ value in ppm.

By the method of Example (II-a-1), and in accordance with the general description of the preparation process e) according to the invention, it is also possible to obtain the compounds of the formula (fi-a) according to the invention listed in Table 8 below:

TABLE 8

(III-a)

| Ex. No. | $Z^2$ | $R^4$ | $R^5$ | $X^3$ | phys. data |
|---|---|---|---|---|---|
| (III-a-2) | 2-Fluorophenyl | —CH$_3$ | —CH$_3$ | Br | MS*: m/e = 259, 262 (M$^+$) |
| (III-a-3) | 4-t-Butylphenyl | —CH$_3$ | —CH$_3$ | Br | MS*: m/e = 297, 299 (M$^+$) |
| (III-a-4) | 3-Trifluoromethylphenyl | —CH$_3$ | —CH$_3$ | Br | MS*: m/e = 309, 311 (M$^+$) |

*Mass spectrum

USE EXAMPLES

Example 1
Pyricularia Test (rice)/Protective

Solvent: 12.5 parts by weight of acetone

Emulsifier: 0.3 part by weight of alkylaryl polyglycol ether

To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed to run off point with the preparation of active compound. After the spray coating has dried on, the plants are inoculated with an aqueous spore suspension of Pyricularia oryzae. The plants are subsequently placed in a greenhouse at 100% relative atmospheric humidity and at 25° C.

Evaluation is carried out 4 days after the inoculation.

0% means an efficacy which corresponds to that of the control, whereas an efficacy of 100% means that no infection is observed.

In this test, for example the following compounds of Preparation Examples 5, 6, 7, 8, 9, 10 and 11 exhibit, at an exemplary active compound concentration of 0.05%, an efficacy of 100%. At the same concentration of active compound, the compound of Preparation Example 1 exhibited an efficacy of 90%.

Example 2
Phytophthora Test (tomato)/Protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Phytophthora infestans.

The plants are then placed in an incubation cabin at approximately 20° C. and 100% relative atmospheric humidity.

Evaluation is carried out 3 days after the inoculation. 0% means an efficacy which corresponds to that of the control, whereas an efficacy of 100% means that no infection is observed.

In this test, for example the following compounds of Preparation Examples 9, 10 and 11 exhibit, at an exemplary active compound application rate of 100 g/ha, an efficacy of 91–93%, compared to the untreated control.

Example 3
Plasmopara Test (grapevines)/Protective

Solvent: 47 parts by weight of acetone

Emulsifier: 3 parts by weight of alkylaryl polyglycol ether

To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Plasmopara viticola and then remain in an incubation cabin at 20° C. and 100% relative atmospheric humidity for 1 day. The plants are subsequently kept in a greenhouse at 21° C. and approximately 90% atmospheric humidity for 5 days. The plants are then moistened and kept in an incubation cabin for 1 day.

Evaluation is carried out 6 days after the inoculation. 0% means an efficacy which corresponds to that of the control, whereas an efficacy of 100% means that no infection is observed.

In this test, for example the following compounds of Preparation Examples 5, 6, 7, 8, 9, 10 and 11 exhibit, at an exemplary active compound application rate of 100 g/ha, an efficacy of 99–100% in comparison to the untreated control.

Example 4
Podosphaera Test (apple)/Protective

Solvent: 47 parts by weight of acetone

Emulsifier: 3 parts by weight of alkylaryl polyglycol ether

To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Podosphaera leucotricha. The plants are then kept in a greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

In this test, for example, the following compounds of Preparation Examples 3 and 9 exhibit, at an exemplary active compound application rate of 10 g/ha, an efficacy of 94–98% in comparison to the untreated control.

Example 5
Sphaerotheca Test (cucumber)/Protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at approximately 23° C. and a relative atmospheric humidity of approximately 70% in the greenhouse.

Evaluation is carried out 10 days after the inoculation. 0% means an efficacy which corresponds to that of the control, whereas an efficacy of 100% means that no infection is observed.

In this test, for example the following compounds of Preparation Examples 2, 3, 5, 6, 7, 9, 10 and 11 exhibit, at an exemplary active compound application rate of 100 g/ha, an efficacy of 92–100% in comparison to the untreated control.

Example 6
Venturia Test (apple)/Protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the causative organism of apple scab Venturia inaequalis and then remain in an incubation cabin at approximately 20° C. and 100% relative atmospheric humidity for 1 day.

The plants are then placed in a greenhouse at approximately 21° C. and a relative atmospheric humidity of approximately 90%.

Evaluation is carried out 12 days after the inoculation. 0% means an efficacy which corresponds to that of the control, whereas an efficacy of 100% means that no infection is observed.

In this test, for example the following compounds of Preparation Examples 1, 3, 5, 6, 7, 9, 10 and 11 exhibit, at an exemplary active compound application rate of 100 g/ha, an efficacy of 94–100% in comparison to the untreated control.

Example 7
Erysiphe Test (barley)/Protective

Solvent: 10 parts by weight of N-methyl-pyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of Erysiphe graminis f.sp. hordei.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infection is observed.

In this test, for example the following compounds of preparation examples 1, 6, 7, 9, 10 and 11 exhibit, at an exemplary active compound application rate of 250 g/ha, an efficacy of 88% in comparison to the untreated control.

What is claimed is:

1. Compounds of the formula (I)

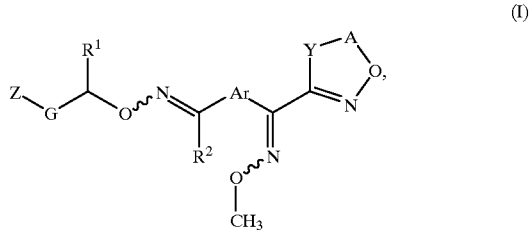

in which

A represents alkanediyl,

Ar represents in each case optionally substituted arylene or heteroarylene,

G represents a single bond, alkanediyl which is optionally interrupted by hetero atoms (but where the carbon atom to which $R^1$ is attached is in each case linked with a carbon atom of the alkanediyl chain) or a grouping

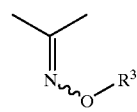

in which $R^3$ represents alkyl, $R^1$ represents hydrogen, cyano or in each case optionally substituted alkyl, alkoxy, alkylthio, alkylamino, dialkylamino or cycloalkyl, $R^2$ represents hydrogen or alkyl, Y represents oxygen, sulphur or —NH— and Z represents in each case optionally substituted alkyl, alkenyl, alkinyl, cycloalkyl, aryl or heterocyclyl.

2. Compounds of the formula (I) according to claim 1 in which

A represents alkanediyl having 1 to 6 carbon atoms,

Ar represents in each case optionally substituted phenylene or naphthylene, represents mono- or bicyclic heteroarylene having in each case 5 or 6 ring members or represents benzo-fused heteroarylene having 5 or 6 ring members at least one of which in each case represents oxygen, sulphur or nitrogen and one or two others optionally represent nitrogen, where the possible substituents are preferably selected from the list below:

halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl having in each case 1 to 6 carbon atoms, in each case straight-chain or branched alkenyl, alkenyloxy or alkinyloxy having in each case 2 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched halogenoalkenyl or halogenoalkenyloxy having in each case 2 to 6 carbon atoms and 1 to 11 identical or different halogen atoms, in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, in each case doubly attached alkylene or dioxyalkylene having in each case 1 to 6 carbon atoms and being in each case optionally mono- or polysubstituted by identical or different substituents selected from the group consisting of halogen, straight-chain or branched alkyl having 1 to 4 carbon atoms and straight-chain or branched halogenoalkyl having 1 to 4 carbon atoms and 1 to 9 identical or different halogen atoms, G represents a single bond, represents alkanediyl having 1 to 5 chain members which is optionally interrupted by one or two heteroatoms (but where the carbon atom to which $R^1$ is attached is in each case linked to a carbon atom of the alkanediyl chain) or a grouping

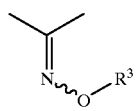

in which
$R^3$ represents alkyl having 1 to 4 carbon atoms,
$R^1$ represents hydrogen, cyano, represents in each case optionally halogen-, cyano- or $C_1$–$C_4$-alkoxy-substituted alkyl, alkoxy, alkylthio, alkylamino or dialkylamino having in each case 1 to 6 carbon atoms in the alkyl groups or represents in each case optionally halogen-, cyano-, carboxyl-, $C_1$–$C_4$-alkyl- or $C_1$–$C_4$-alkoxy-carbonyl-substituted cycloalkyl having 3 to 6 carbon atoms,
$R^2$ represents hydrogen or alkyl having 1 to 4 carbon atoms,
Y represents oxygen, sulphur or —NH— and
Z represents alkyl having 1 to 8 carbon atoms which is optionally mono- or polysubstituted by an identical or different substituent selected from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkyl-sulphonyl (each of which may optionally be substituted by halogen);
represents in each case optionally halogen-substituted alkenyl or alkinyl having in each case up to 8 carbon atoms;
represents cycloalkyl having 3 to 6 carbon atoms which is in each case optionally mono- or polysubstituted by identical or different substituents selected from the group consisting of halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogeno-alkoxy), $C_1$–$C_4$-alkyl and $C_1$–$C_4$-alkoxy-carbonyl;
or represents phenyl, naphthyl, each of which is optionally mono- or polysubstituted by identical or differ-
ent substituents, or represents heterocyclyl having 3 to 7 ring members at least one of which represents oxygen, sulphur or nitrogen and one or two others optionally represent nitrogen, where the possible substituents are preferably selected from the list below:
halogen, cyano, nitro, amino, hydroxyl, formyl, carboxyl, carbamoyl, thiocarbamoyl;
in each case straight-chain or branched alkyl, alkoxy, alkylthio, alkylsulphinyl or alkylsulphonyl having in each case 1 to 6 carbon atoms;
in each case straight-chain or branched alkenyl or alkenyloxy having in each case 2 to 6 carbon atoms;
in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
in each case straight-chain or branched halogenoalkenyl or halogenoalkenyloxy having in each case 2 to 6 carbon atoms and 1 to 11 identical or different halogen atoms;
in each case straight-chain or branched alkylamino, dialkylamino, alkylcarbonyl, alkylcarbonyloxy, alkoxycarbonyl or alkylsulphonyloxy having in each case 1 to 6 carbon atoms in the individual alkyl moieties;
in each case doubly attached alkylene or dioxyalkylene having in each case 1 to 6 carbon atoms and being in each case optionally mono- or polysubstituted by identical or different substituents selected from the group consisting of halogen, straight-chain or branched alkyl having 1 to 4 carbon atoms and straight-chain or branched halogenoalkyl having from 1 to 4 carbon atoms and 1 to 9 identical or different halogen atoms;
cycloalkyl having 3 to 6 carbon atoms; heterocyclyl or heterocyclyl-methyl having in each case 3 to 7 ring members, 1 to 3 of which are in each case identical or different heteroatoms—in particular nitrogen, oxygen and/or sulphur—or a grouping

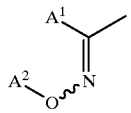

in which
$A^1$ represents alkyl having 1 to 4 carbon atoms or cycloalkyl having 1 to 6 carbon atoms and
$A^2$ represents optionally cyano-, alkoxy-, alkylthio-, alkylamino-, dialkylamino- or phenyl-substituted alkyl having 1 to 4 carbon atoms, alkenyl or alkinyl having in each case 2 to 4 carbon atoms.

3. Compounds of the formula (I) according to claim 1 in which
A represents methylene, ethane-1,1-diyl, ethane-1,2-diyl, propane-1,1-diyl, propane-1,2-diyl, propane-1,3-diyl, propane-2,2-diyl, butane-1,2-diyl, butane-1,3-diyl or butane-2,3-diyl,
Ar represents ortho-, meta- or para-phenylene, furandiyl, thiophenediyl, pyrrolediyl, pyrazolediyl, triazolediyl, oxazolediyl, isoxazolediyl, thiazolediyl, isothiazolediyl, oxadiazolediyl, thiadiazolediyl, pyridinediyl (in particular pyridine-2,3-diyl), pyrimidinediyl, pyridazinediyl, pyrazinediyl, 1,3,4-triazinediyl or 1,2,3-triazinediyl, each of which is optionally mono- or disubstituted by fluorine, chlorine, cyano, methyl, ethyl, cyclopropyl, trifluoromethyl, methoxy, ethoxy, methylthio, methylsulphinyl or methylsulphonyl, G represents a single bond, methylene, ethane-1,2-diyl, —O—CH$_2$— or a grouping

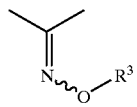

in which

R$^3$ represents methyl, ethyl, n- or i-propyl,

R$^1$ represents hydrogen, cyano, methyl, ethyl or cyclopropyl,

R$^2$ represents hydrogen or methyl,

Y represents oxygen, sulphur or —NH— and

Z represents phenyl, 1,2,4-thiadiazolyl, 1,3,4-thiadiazolyl, 1,2,4-oxa-diazolyl, 1,3,4-oxadiazolyl, pyridinyl, pyrimidyl, pyridazinyl, pyrazinyl, 1,2,3-triazinyl, 1,2,4-triazinyl, 1,3,5-triazinyl or 5,6-dihydro-1,4,2-dioxazinyl, each of which is optionally mono- to trisubstituted by identical or different substituents, where the possible substituents are preferably selected from the list below:

fluorine, chlorine, bromine, cyano, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, in each case doubly attached methylenedioxy, ethylenedioxy, each of which is optionally mono- to tetrasubstituted by identical or different substituents selected from the group consisting of fluorine, chlorine, methyl, trifluoromethyl and ethyl, a grouping

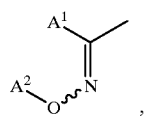

where

A$^1$ represents methyl, ethyl, n- or i-propyl, n-, i-, s- or t-butyl, cyclopropyl or cyclobutyl and A$^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

4. Compounds of the formula (I) according to claim 1, in which

A represents methylene, ethane-1,1-diyl, ethane-1,2-diyl, propane-1,1-diyl, propane-1,2-diyl, propane-1,3-diyl, propane-2,2-diyl, butane-1,2-diyl, butane-1,3-diyl or butane-2,3-diyl, Ar represents ortho-phenylene, pyridine-2,3-diyl or thiophene-2,3-diyl, G represents a single bond, methylene, ethane-1,2-diyl, —O—CH$_2$— or a grouping

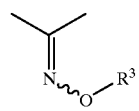

in which

R$^3$ represents methyl,

R$^1$ represents methyl,

R$^2$ represents hydrogen,

Y represents oxygen, sulphur or —NH— and

Z represents phenyl, pyridyl, pyrimidyl, thienyl or 5,6-dihydro-1,4,2-dioxazinyl, each of which is optionally mono- to trisubstituted by identical or different substituents, where the possible substituents are preferably selected from those below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, in each case doubly attached methylenedioxy or ethylenedioxy, each of which is optionally mono- to tetrasubstituted by identical or different substituents selected from the group consisting of fluorine, chlorine, methyl, trifluoromethyl and ethyl or a grouping

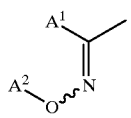

in which

A$^1$ represents methyl, ethyl, n- or i-propyl, n-, i-, s- or t-butyl, cyclopropyl or cyclobutyl and A$^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

5. Process for preparing compounds of the formula (I) as defined in claim 1, characterized in that oximes of the general formula (II)

(II)

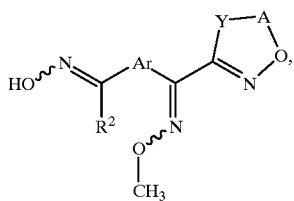

in which

A, Ar, Y and R² are as defined in claim 1, are reacted with an alkylating agent of the general formula (III)

(III)

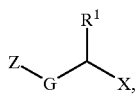

in which

G, R¹ and Z are as defined above and

X represents halogen, alkylsulphonyloxy or optionally substituted arylsulphonyloxy, if appropriate in the presence of a diluent and if appropriate in the presence of an acid acceptor.

6. Process for preparing pesticides, characterized in that compounds of the formula (I) according to claim 1 are mixed with extenders and/or surfactants.

7. Compounds of the formula (II)

(II)

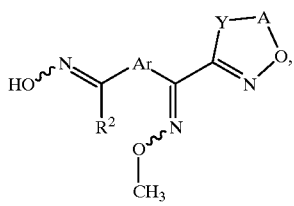

in which

R², Ar, Y and A are as defined in claim 1.

8. Compounds of the formula (IV)

(IV)

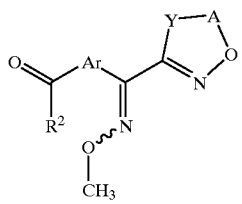

in which

R², Ar, Y and A are as defined in claim 1.

9. Compounds of the formula (V)

(V)

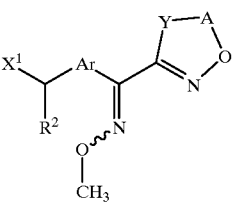

in which

X¹, R², Ar, Y and A are as defined in claim 1.

10. Compounds of the formula (III-a), (III-a)

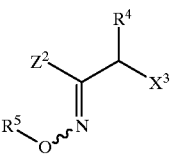

in which

R⁴ represents alkyl or cycloalkyl,

R⁵ represents alkyl,

X³ represents halogen and

Z² represents optionally substituted aryl or heterocyclyl.

11. Compounds of the formula (III-a) according to claim 10, in which

R⁴ represents alkyl having 1 to 4 carbon atoms or cycloalkyl having 3 to 6 carbon atoms, R⁵ represents alkyl having 1 to 4 carbon atoms, X³ represents chlorine, bromine or iodine and Z² represents phenyl, naphthyl, each of which is optionally mono- or polysubstituted by identical or different substituents, or represents heterocyclyl having 3 to 7 ring members at least one of which represents oxygen, sulphur or nitrogen and one or two others optionally represent nitrogen, where the possible substituents are preferably selected from the list below:

halogen, cyano, nitro, amino, hydroxyl, formyl, carboxyl, carbamoyl, thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched halogenalkyl, halogenalkoxy, halogenoalkylthio, halogenalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms; in each case straight-chain or branched alkylamino, dialkylamino, alkylcarbonyl, alkylcarbonyloxy, alkoxycarbonyl or alkylsulphonyloxy having in each case 1 to 6 carbon atoms in the individual alkyl moieties;

in each case doubly attached alkylene or dioxyalkylene having in each case 1 to 6 carbon atoms and being in each case optionally mono- or polysubstituted by identical or different substituents selected from the group consisting of halogen, straight-chain or branched alkyl having 1 to 4 carbon atoms and straight-chain or branched halogenoalkyl having from 1 to 4 carbon atoms and 1 to 9 identical or different halogen atoms;

cycloalkyl having 3 to 6 carbon atoms;

heterocyclyl or heterocyclyl-methyl having in each case 3 to 7 ring members, 1 to 3 of which are in each case identical or different heteroatoms—in particular nitrogen, oxygen and/or sulphur—or a grouping

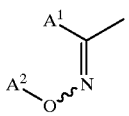

in which

A³ represents alkyl having 1 to 4 carbon atoms or cycloalkyl having 1 to 6 carbon atoms and A⁴ represents optionally cyano-, alkoxy-, alkylthio-, alkylamino-, dialkylamino- or phenyl-substituted alkyl having 1 to 4 carbon atoms, alkenyl or alkinyl having in each case 2 to 4 carbon atoms.

12. Compounds of the formula (III-a) according to claim 10 in which

R⁴ represents methyl, ethyl or cyclopropyl,

R⁵ represents methyl or ethyl,

X³ represents chlorine or bromine and

Z² represents phenyl, pyridyl, pyrimidyl or thienyl, each of which is optionally mono- to trisubstituted by identical or different substituents, where the possible substituents are preferably selected from the list below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, in each case doubly attached methylenedioxy or ethylenedioxy, each of which is optionally mono- to tetrasubstituted by identical or different substituents selected from the group consisting of fluorine, chlorine, methyl, trifluoromethyl and ethyl, or a grouping

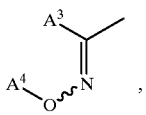

in which

A³ represents methyl, ethyl, n- or i-propyl, n-, i-, s- or t-butyl, cyclopropyl or cyclobutyl and A⁴ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

13. Process for preparing compounds of the formula (III-a) as defined in claim 10, characterized in that halogenoketones of the general formula (VIII)

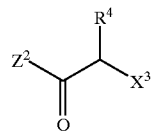

(VIII)

in which

R⁴, X³ and Z² are as defined above, are reacted with hydroxylamine or a salt thereof, if appropriate in the presence of a diluent, preferably an an alcohol, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water and if appropriate in the presence of a base, preferably an alkaline earth metal or alkali metal hydroxide, alkoxide, acetate, carbonate or bicarbonate, such as, for example, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, or a tertiary amine, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

14. A pesticidal composition comprising a pesticidally effective amount of at least one compound of the formula (I) according to claim 1 and an extender and/or surfactant.

15. A method for controlling a pest comprising applying to said pest and/or its habitat a pesticidally effective amount of at least one compound of the formula (I) according to claim 1.

\* \* \* \* \*

UNITED STATES PATENT AND TRADEMARK OFFICE
CERTIFICATE OF CORRECTION

PATENT NO.   : 6,271,226 B1                                               Page 1 of 1
DATED        : August 7, 2001
INVENTOR(S)  : Bernd-Wieland Kruger et al.

It is certified that error appears in the above-identified patent and that said Letters Patent is hereby corrected as shown below:

<u>Title page,</u>
Item [75], Inventors, change the place of the first inventor's residence from "Gladbach, Germany" to -- Bergisch Gladbach, Germany --

<u>Column 36,</u>
Line 14, change the sentence from "$X^1$, $R^2$, Ar, Y and A are as defined in claim 1." to -- $R^2$, Ar, Y and A are as defined in claim 1 and $X^1$ represents halogen --

<u>Column 38,</u>
Lines 29 and 30, should read -- if appropriate in the presence of a diluent, preferably an alcohol, such as… -- (delete the extra word "an" which was used twice)

Signed and Sealed this

Sixteenth Day of September, 2003

JAMES E. ROGAN
*Director of the United States Patent and Trademark Office*